US010302460B2

(12) United States Patent
Varga et al.

(10) Patent No.: US 10,302,460 B2
(45) Date of Patent: May 28, 2019

(54) LIQUID METAL SENSOR

(71) Applicant: Microsoft Technology Licensing, LLC, Redmond, WA (US)

(72) Inventors: Matija Varga, Zurich (CH); Siyuan Ma, Redmond, WA (US); James David Holbery, Bellevue, WA (US); Collin Alexander Ladd, Sammamish, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 15/611,141

(22) Filed: Jun. 1, 2017

(65) Prior Publication Data
US 2018/0120130 A1 May 3, 2018

Related U.S. Application Data

(60) Provisional application No. 62/414,621, filed on Oct. 28, 2016.

(51) Int. Cl.
*G01D 5/241* (2006.01)
*A61B 5/00* (2006.01)
(Continued)

(52) U.S. Cl.
CPC ........... *G01D 5/241* (2013.01); *A61B 5/0015* (2013.01); *A61B 5/1126* (2013.01);
(Continued)

(58) Field of Classification Search
CPC .... G01D 5/24; G01P 15/125; G01C 2009/182
See application file for complete search history.

(56) References Cited

U.S. PATENT DOCUMENTS 9,851,857 B2 * 12/2017 Kim ..................... G01L 9/0072
2007/0125178 A1 6/2007 Rosenau et al.
(Continued)

FOREIGN PATENT DOCUMENTS

WO 2012050938 A2 4/2012
WO 2015157272 A1 10/2015

OTHER PUBLICATIONS

Koo, et al., "Manipulating Liquid Metal Droplets in Microfluidic Channels with Minimized Skin Residues Toward Tunable RF Applications", In Journal of Microelectromechanical Systems. vol. 24, Issue 4, Aug. 1, 2015, pp. 1069-1076.
(Continued)

*Primary Examiner* — Giovanni Astacio-Oquendo
*Assistant Examiner* — Alvaro E Fortich
(74) *Attorney, Agent, or Firm* — Alleman Hall Creasman & Tuttle LLP

(57) ABSTRACT

Described herein is a sensor including a sensing electrode structure and a motion-responsive structure in capacitive communication with the sensing electrode structure, the sensing electrode structure and the motion-responsive structure being separated by a first dielectric layer, the motion-responsive structure comprising a liquid metal mass within a matrix in which the liquid metal mass is movable based upon movement of the sensor, and the sensing electrode structure comprising a first electrode, and a second electrode spaced from the first electrode to form a capacitor.

9 Claims, 10 Drawing Sheets

(51) Int. Cl.
    *A61B 5/11* (2006.01)
    *G01P 15/125* (2006.01)
    *H01G 5/013* (2006.01)
    *G01C 9/18* (2006.01)

(52) U.S. Cl.
    CPC .............. *A61B 5/6806* (2013.01); *G01C 9/18* (2013.01); *G01P 15/125* (2013.01); *H01G 5/0132* (2013.01); *A61B 2562/028* (2013.01); *A61B 2562/0214* (2013.01); *A61B 2562/0219* (2013.01); *A61B 2562/12* (2013.01); *A61B 2562/164* (2013.01); *G01C 2009/182* (2013.01)

(56) References Cited

U.S. PATENT DOCUMENTS

| | | | |
|---|---|---|---|
| 2008/0185174 | A1 | 8/2008 | Bedinger et al. |
| 2010/0304013 | A1* | 12/2010 | Wang ...................... G06F 3/044 427/58 |
| 2013/0000117 | A1 | 1/2013 | Baskaran et al. |
| 2014/0174189 | A1* | 6/2014 | Pan ........................ G01L 9/0072 73/724 |
| 2015/0340970 | A1 | 11/2015 | Kwon et al. |
| 2016/0224152 | A1 | 8/2016 | Kim et al. |

OTHER PUBLICATIONS

Lin, et al., "Micro-Impedance Inclinometer with Wide-Angle Measuring Capability and No Damping Effect", In Proceeding of Sensors and Actuators A: Physical, vol. 143, Issue 1, Mar. 20, 2008, pp. 113-119.

"International Search Report and Written Opinion Issued in PCT Application No. PCT/US2017/057782", dated Jun. 8, 2018, 19 Pages.

Rahman, et al., "Electrically Actuated Liquid Metal for Reconfigurable RF Devices", In IEEE/ACES International Conference on Wireless Information Technology and Systems (ICWITS) and Applied Computational Electromagnetics (ACES), Mar. 13, 2016, 9 Pages.

Ryosuke, et al., "Highly Stretchable Global and Distributed Local Strain Sensing Line Using GaInSn Electrodes for Wearable Electronics", In Proceeding of Advanced Functional Materials, vol. 25, May 7, 2015, pp. 3806-3813.

Shuangfeng, L., et al., "Design and Fabrication of a New Miniaturized Capacitive Accelerometer", In Proceeding of Sensors and Actuators A : Physical, vol. 147, Issue1, Sep. 15, 2008, pp. 70-74.

Khondoker, et al., "Fabrication methods and applications of microstructured gallium based liquid metal alloys", In Journal of Smart Materials and Structures, vol. 25, No. 9, Aug. 8, 2016, pp. 1-24.

Pekas, et al., "Electrostatic actuator with liquid metal—elastomer compliant electrodes used for on-chip microvalving", In Journal of Micromechanics and Microengineering vol. 22, No. 9, Jul. 26, 2012, pp. 1-7.

Hyun-Joong, et al., "A multiaxial stretchable interconnect using liquid-alloy-filled elastomeric microchannel", In Journal of Applied Physics Letters vol. 92, No. 1, Jan. 2008, 4 pages.

Kim, et al., "Stretchable Microfluidic Radiofrequency Antennas", In Journal of Advanced materials, vol. 22, Issue 25, Jul. 2010, 5 pages.

Kramer, et al., "Masked Deposition of Gallium-Indium Alloys for Liquid-Embedded Elastomer Conductors", In Journal of Advanced Functional Materials vol. 23, No. 42, Nov. 13, 2013, pp. 1-5.

Dickey, et al., "Eutectic Gallium-Indium (EGaIn): A Liquid Metal Alloy for the Formation of Stable Structures in Microchannels at Room Temperature", In Journal of Advanced Functional Materials, vol. 18, No. 7, Apr. 11, 2008, 4 pages.

Lipomi, et al., "Skin-like pressure and strain sensors based on transparent elastic films of carbon nanotubes", In Journal of Nature Nanotechnology, vol. 6, Issue 12, Oct. 23, 2011, pp. 788-792.

Chiechi, et al., "Eutectic Gallium-Indium (EGaIn): A Moldable Liquid Metal for Electrical Characterization of Self-Assembled Monolayers", In Journal of Angewandte Chemie, Nov. 23, 2007, 4 pages.

Dickey, Michael D., "Emerging Applications of Liquid Metals Featuring Surface Oxides", In Journal of ACS applied materials & interfaces, vol. 6, Issue 21, Oct. 6, 2014, 4 pages.

Joshipura, et al., "Methods to pattern liquid metals", In Journal of Materials Chemistry, Issue 16, Mar. 31, 2015, 4 pages.

Hirsch, et al., "Intrinsically Stretchable Biphasic (Solid—Liquid) Thin Metal Films", In Journal of Advanced Materials, Feb. 1, 2016, pp. 1-6.

Huang, et al., "Materials and Designs for Wireless Epidermal Sensors of Hydration and Strain", In Journal of Advanced Functional Materials vol. 24, No. 25, Jul. 1, 2014, pp. 1-9.

Kaltenbrunner, et al., "An ultra-lightweight design for imperceptible plastic electronics", In Journal of Nature, vol. 499, Issue 7459, Jul. 25, 2013, pp. 458-465.

\* cited by examiner

LIQUID METAL SENSOR

CROSS REFERENCE TO RELATED APPLICATIONS

This application claims priority to U.S. Provisional Patent Application No. 62/414,621 filed Oct. 28, 2016, the entirety of which is hereby incorporated herein by reference.

BACKGROUND

Sensors may use capacitive sensing to detect various physical states and changes. Examples include, but are not limited to, detecting proximity, position, displacement, humidity, fluid level, and acceleration.

SUMMARY

Examples are disclosed that relate to sensors that utilize liquid metal conductors. One example provides a sensor including a sensing electrode structure and a motion-responsive structure in capacitive communication with the sensing electrode structure, the sensing electrode structure and the motion-responsive structure being separated by a dielectric layer. The motion-responsive structure comprises a liquid metal mass within a matrix in which the liquid metal mass is movable based upon movement of the sensor, and the sensing electrode structure comprises a first electrode and a second electrode spaced from the first electrode to form a capacitor.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

This disclosure provides examples of sensors utilizing liquid metal elements, and methods of making such sensors. As described in more detail below, the disclosed examples may be manufactured using low-cost processes (e.g. processes which do not require vacuum deposition process or photolithography steps), and may be configured to be stretchable and wearable on skin to detect motion and other physical states. Briefly, the disclosed motion sensors include a sensing electrode structure comprising one or more pairs of sensing electrodes that form one or more capacitors, wherein the electrodes are formed from a liquid metal, such as a gallium-indium containing composition. When encapsulated in an elastomeric material, such a sensor may be stretchable and bendable. This may allow the sensor to be attached to skin and/or used in other settings where a sensed surface may stretch, contract, and/or otherwise deform during sensor use.

As described in more detail below, in some examples a sensor may include a motion-responsive structure that is electrically insulated from, but capacitively coupled with, the sensing electrodes. The motion-responsive structure includes a liquid metal mass, such as a droplet, contained within a matrix, such as a liquid matrix, in which the liquid metal droplet is movable based upon movement of the sensor. As the droplet moves in response to sensor changes, the capacitance of the electrode pairs changes due to the change in the electrical permittivity in the region of the electrodes, thereby permitting motion, stretch/stress, pressure, etc. to be predictably detected. While described in the context of a motion sensor, the disclosed example sensors may be adapted to sense any other condition than motion that can be sensed capacitively, such as humidity, temperature, and gases (e.g. carbon monoxide and/or ammonia). In some such examples, the motion-responsive structure may be omitted, and other suitable structures that respond to the condition being sensed may be included. The liquid metal material may be configured to be liquid at room temperature, or at any other suitable operating temperature.

Figure 1A:
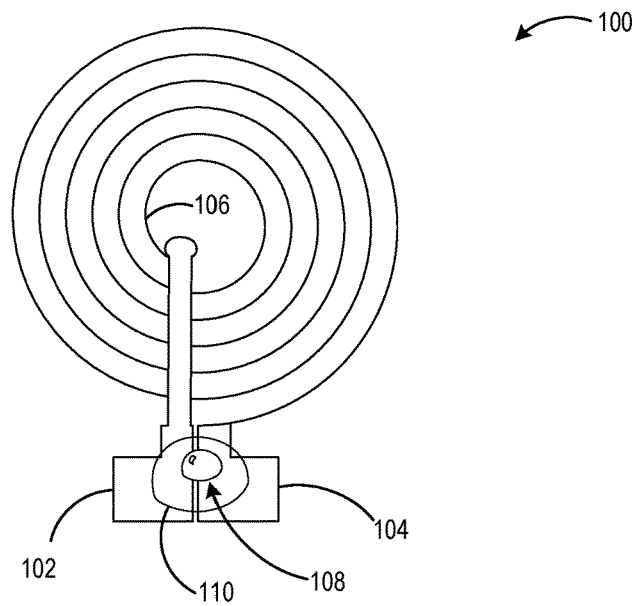
FIGS. 1A and 1B show an example sensor.
Figure 1B:
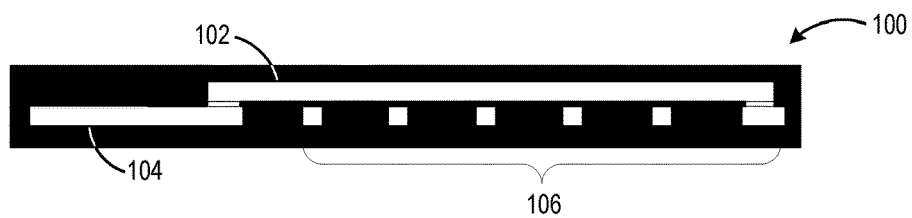

FIG. 1A shows an example sensor 100 formed using liquid metal in accordance with an embodiment of this disclosure, and FIG. 1B shows a side view of a portion of sensor 100. The sensor 100 includes a first sensing electrode 102, a second sensing electrode 104, and a radiofrequency (RF) antenna 106 structure in electrical communication with the first sensing electrode 102 and the second sensing electrode 104. In the depicted example, these structures are all formed from a liquid metal, and are encapsulated with an elastomeric material to permit the sensor to stretch and bend. The liquid metal can deform and flow during such stretching and bending so that a conductive path is maintained without breaking the circuit. In another example, the RF antenna may be omitted, such as where direct electrical connections to sensor electrodes are used.

The sensor 100 also includes a liquid metal droplet 108 contained in a matrix 110 within which the liquid metal droplet can flow. The liquid metal droplet 108 is located above the first sensing electrode 102 and the second sensing electrode 104. As the sensor moves (e.g. when the sensor tilts), the metal droplet 108 can shift in position relative to the first sensing electrode 102 and the second sensing electrode 104. The shifting changes the electrical permittivity in the region of the first sensing electrode 102 and the second sensing electrode 104, which changes the capacitance of the first sensing electrode 102 and the second sensing electrode 104. This change in capacitance can thus be detected as a motion signal.

Figure 2:
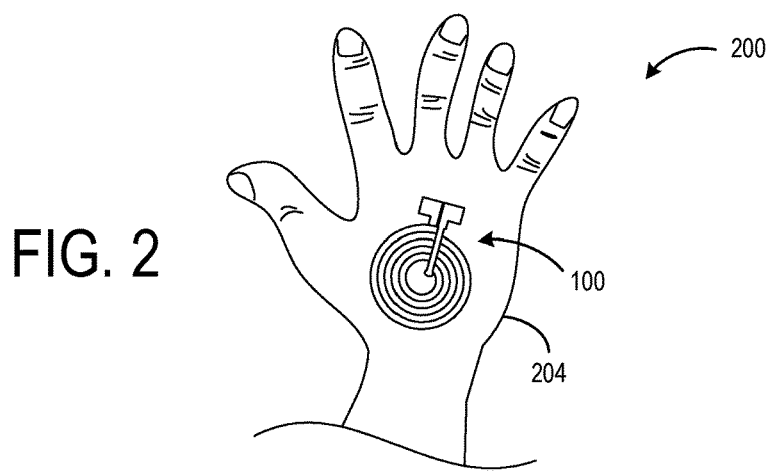
FIG. 2 shows an example use scenario for the sensor of FIGS. 1A and 1B.

FIG. 2 shows an example use scenario 200 for sensor 100. In this scenario, the liquid metal motion sensor 100 is attached to a hand 204 of a person. As the sensor 100 is passive, the sensor may be powered/read by a coil (not shown), for example, that is integrated within clothing worn by the user. As a more specific example, the sensor placed as shown in FIG. 2 may be powered/read by a coil contained in a glove. The sensor 100 may be placed on other parts of the body and powered/read with coils located at corresponding locations in other articles of clothing. For example, a sensor 100 placed on the thigh may be read with a coil located in pants, leggings or other suitable garment.

Figure 3A:
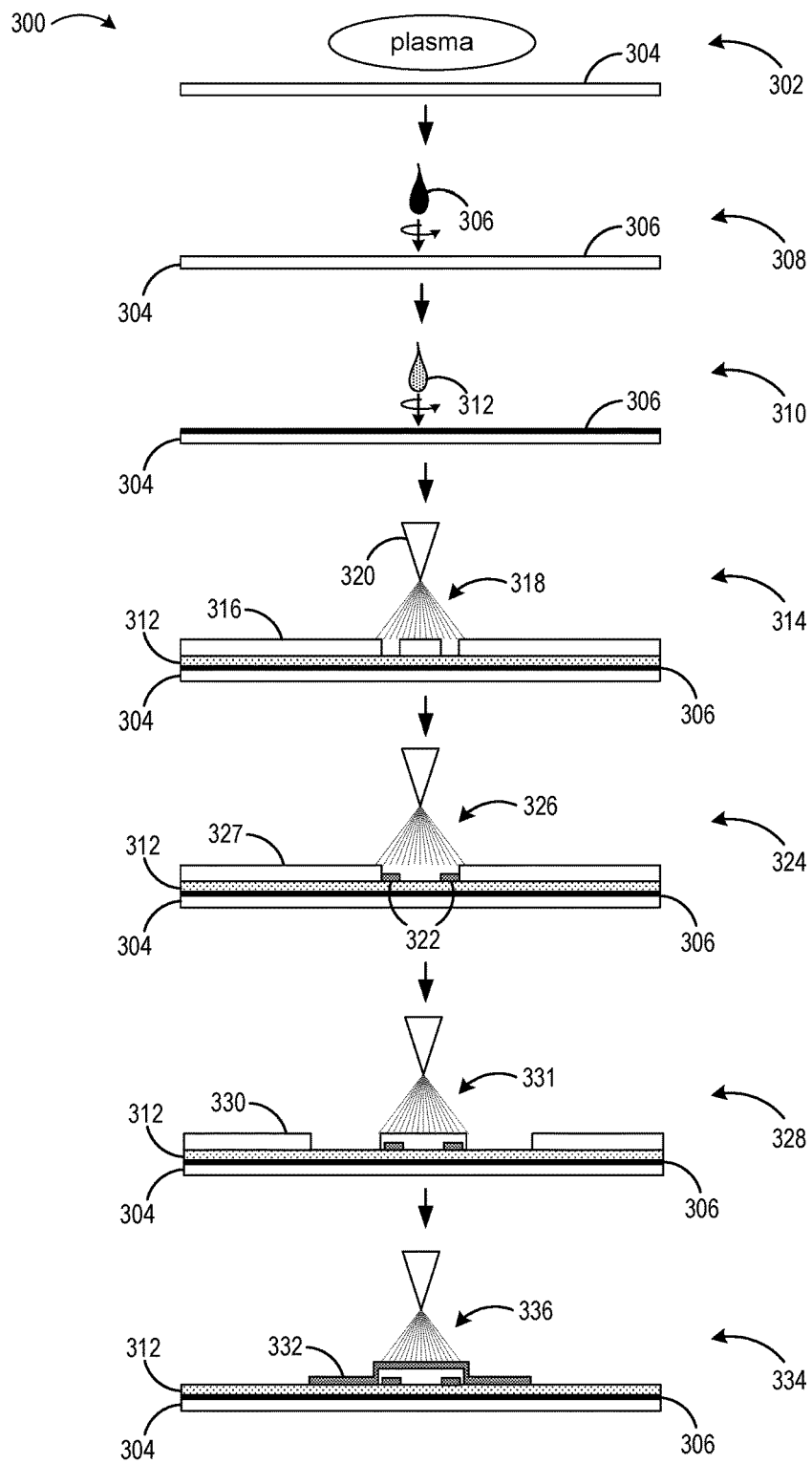
FIGS. 3A and 3B show an example method of making a sensor comprising liquid metal.
Figure 3B:
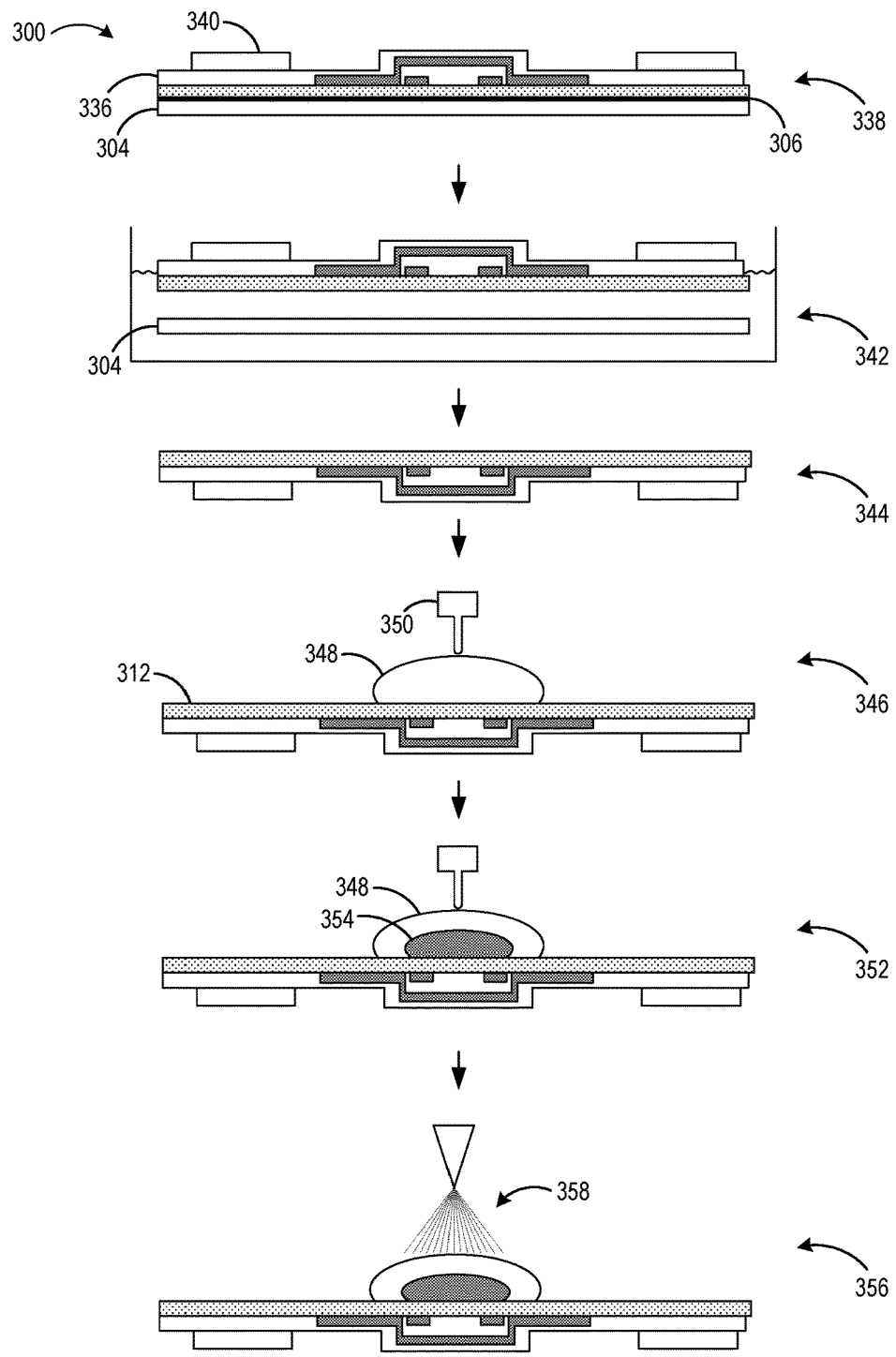

FIGS. 3A and 3B schematically illustrate an example method 300 of forming a motion sensor such as sensor 100, and also illustrate structures that are formed throughout the method. More specifically, FIG. 3A illustrates the formation of a sensing electrode structure, and FIG. 3B illustrates the formation of a motion-responsive structure that varies the capacitance of the sensing electrode structure based upon sensor motion. It will be understood that the steps shown and conditions described with regard to method 300 are non-limiting in nature and that any other suitable processes and/or orders in which processes are performed may be used to form liquid metal sensors in other examples.

At 302, a support structure 304, such as a silicon wafer or other suitable support, is treated with an ionized gas or plasma. For example, an $O_2$ plasma may be applied for 4 minutes at 400 millitorr. Next, a sacrificial layer 306 is spin coated onto the silicon wafer 304, as shown at 308. As one example, the sacrificial layer 306 may be formed from polydiallyldimethylammonium chloride, and may be spin coated onto the substrate and then baked to remove solvent. The sacrificial layer then may be rinsed with deionized water or otherwise cleaned of surface impurities. Next, at 310, a dielectric material 312, such as silicone rubber, is spin coated over the sacrificial layer 306. As an example, Elastosil P7670A+B(1:1) (available from Wacker Chemie AG of Munich, Germany) may be spun on and then cured at 80 degrees C. for 1 minute.

Next, at 314, a first mask 316 is applied to the dielectric layer 312, and a liquid metal 318 is sprayed over the first mask 316 with a nozzle 320 to pattern a first liquid metal electrode 322 of a sensor capacitor. Any suitable liquid metal may be used, including but not limited to various alloys of gallium and indium. The mask used to pattern the electrodes may be a micro-machined or laser-cut stencil, or may take any other suitable form. In other examples, the liquid metal may be applied using direct printing, filling of microfluidic channels via an applied vacuum, screen printing, inkjet printing or other technique.

Figure 9C:
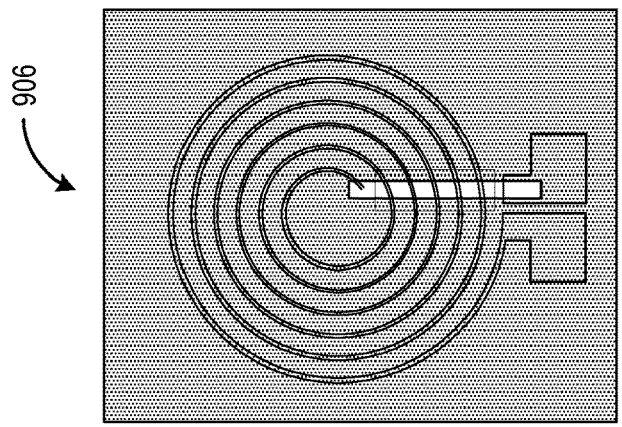
FIGS. 9A-C show example masks used to form layers of the sensor of FIGS. 1A-1B.
Figure 9B:
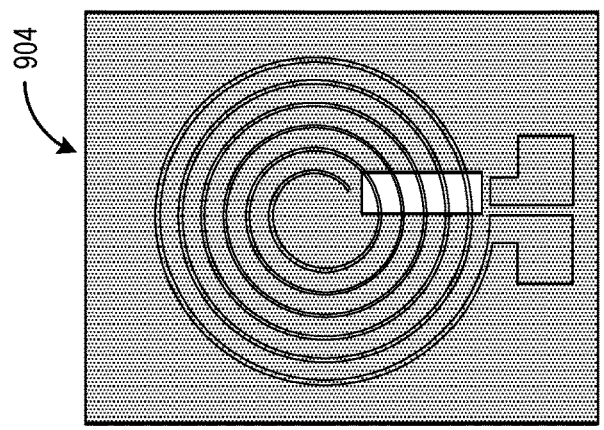
Figure 9A:
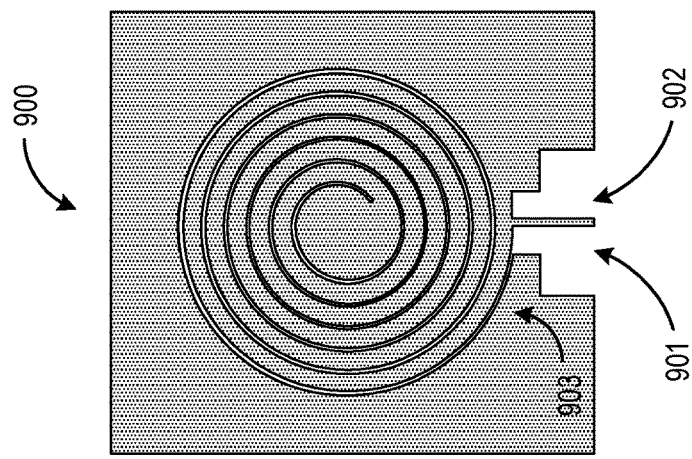

FIGS. 9A-C show examples masks that may be used in forming sensor 100. For example, when forming sensor 100, the first mask 316 shown at step 314 may take the form of mask 900 of FIG. 10A. With this mask, both first and second electrodes of a sensor capacitor, as well as the RF antenna, are formed via the first mask 316, respectively via structures 901, 902, and 903 and then later masking steps are used to form an insulating bridge and an electrical connection to the second electrode, as described in more detail below.

At 324, a second dielectric layer 326 is applied. In the depicted example, the second dielectric layer 326 is formed by spray coating using another mask 327. The second mask 327 may take the form of mask 904 of FIG. 9B when forming sensor 100—in this instance, the second mask is used to build a dielectric bridge across most coils of the RF antenna to allow connection of one end of the RF antenna to the second electrode. Any suitable dielectric material may be used. One example comprises silicone rubber, such as that sold under the name DragonSkin 10 by Smooth-On Inc. of Macungie, Pa., USA (e.g. 1:1 solution by volume in hexane). A solution of the dielectric material is sprayed over the first liquid metal electrode 322, and heated to 80 degrees Celsius for 1 minute to harden the dielectric material. Next, at 328, a third mask 330 is applied, and additional liquid metal is applied by spray coating, as indicated at 331. The third mask 330 may take the form of mask 906 of FIG. 9C when forming sensor 100. In this example, the third mask is used to deposit a liquid metal conductive bridge across the dielectric bridge previously formed to connect an inner terminal of the RF antenna to the second electrode. In other examples, any other suitable number of and configurations of masks may be used, or may be omitted entirely (e.g. where the liquid metal is printed).

At 334, a first passivating layer 336 is applied over the second liquid metal electrode 332. Any suitable material may be used as the first passivating layer, including but not limited to silicone rubber, as described above.

FIG. 3B illustrates, at 338, the structure obtained after a supporting frame 340 is added to the structure created at process 334. To form the structure shown at 338, the supporting frame 340 is first adhered to passivating layer 336, and then the sacrificial layer 306 is dissolved in water at 342, thus releasing the support structure 304. After release, the remaining structure is flipped over, at 344. At 346, a droplet of a matrix material 348, e.g. glycerol, various surfactants, or other suitable materials that allow the liquid metal droplet to interface with the dielectric layer 312 without sticking, is dispensed, e.g. via a syringe dispenser 350, onto the dielectric layer 312 opposite the first and second electrodes. At 352, a liquid metal droplet 354, e.g. gallium indium, is dispensed within the matrix 348. The matrix 348 may functionalize the surface of the liquid metal droplet 354 and control adhesion of the liquid metal, so that the liquid metal droplet 354 may move in response to motion of the sensor. Finally, at 356, a second passivating layer 358 is applied over the matrix 348 (e.g. by spraying or other suitable method), forming the sensor. The moveable liquid metal mass 354 over the first and second liquid metal electrodes 322, 332, separated by a dielectric layer 312, act together as a variable capacitor for capacitive sensing.

Figure 4A:
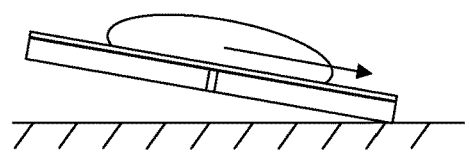
FIG. 4A schematically shows a side view of a liquid metal droplet moving over two capacitor plates of an example sensor, and FIG. 4B schematically shows a top view of the droplet over the plates.
Figure 4B:
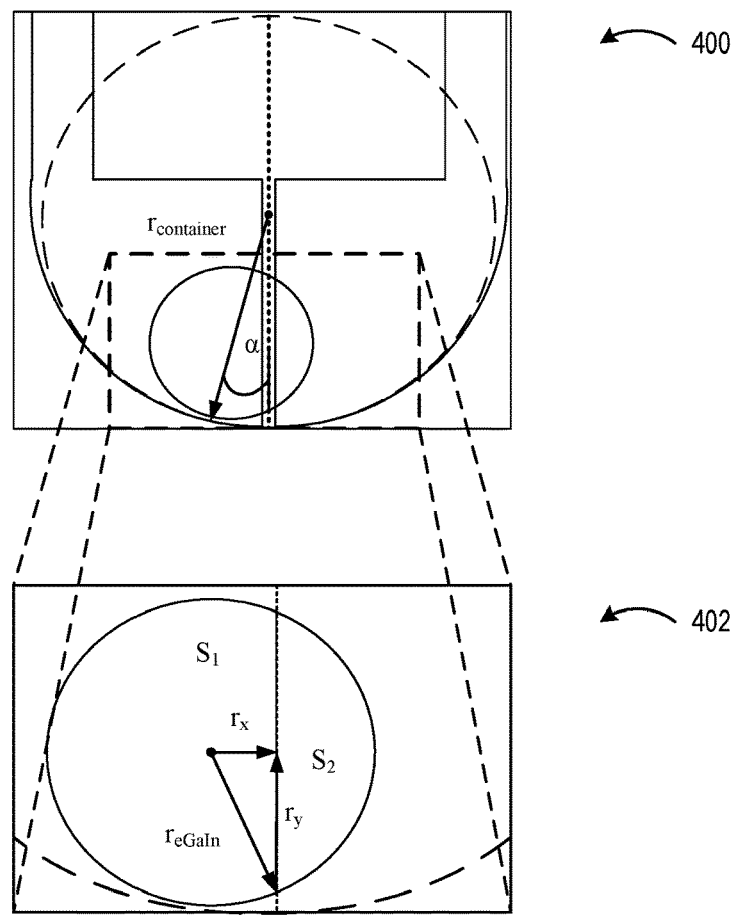

FIG. 4A shows a schematic view of a liquid metal droplet sliding over two metal plates acting as capacitor electrodes, and FIG. 4B shows a top view representation 400 and magnified view 402 of the liquid metal droplet within a matrix over the two metal plates. In these FIGS., $S_1$ is an overlap area of the liquid metal droplet over a first metal plate, $S_2$ is an overlap area of the liquid metal droplet over a second metal plate, angle $\alpha$ is the angle of the liquid metal drop with respect to a center line bisecting the matrix and the two metal plates, $r_{container}$ is the radius of the matrix containing the liquid metal droplet, $r_{eGaIn}$ is the radius of the liquid metal droplet (1.5 mm as an example), $r_x$ is the variable length of the distance between a center of the liquid metal droplet and the center of the two metal plates, and $r_y$ is the variable length of the triangle leg joining $r_x$ and $r_{eGaIn}$.

Figure 10:
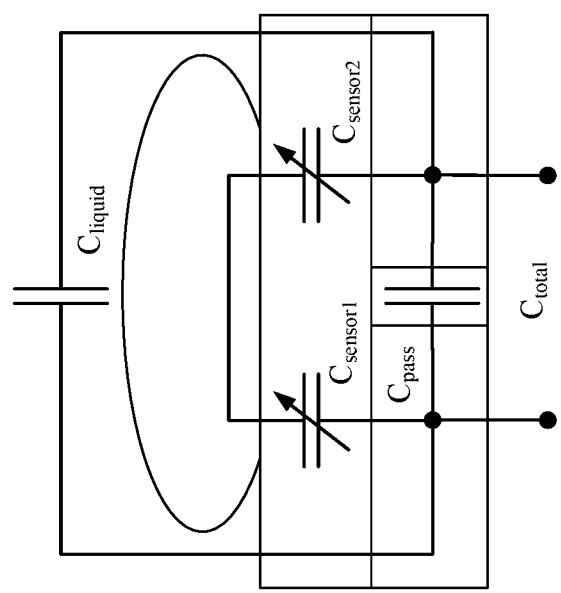
FIG. 10 schematically shows an electrical schematic representation of an example sensor.

FIG. 10 schematically illustrates an electrical configuration of this arrangement. $C_{pass}$ is the passivation between the two electrodes, $C_{liquid}$ is capacitance of the liquid matrix, $C_{sensor1}$ and $C_{sensor2}$ are capacitances corresponding to capacitances $C_1$ and $C_2$ as described above, and $C_{total}$ corresponds to the total capacitance of the sensor. $C_{pass}$ and $C_{liquid}$ are capacitances that may be accounted for in simulations. The following equations may be used to define the variables shown.

$$C_{total} = \frac{C_{sensor1} C_{sensor2}}{C_{sensor1} + C_{sensor2}} + C_{pass} + C_{liquid} \quad (1)$$

$$> \frac{\varepsilon_0 \varepsilon_r}{t} \frac{S_1 S_2}{S} = \frac{\varepsilon_0 \varepsilon_r}{t} \frac{(S - S_2) S_2}{S} = C'_{total}, \quad (2)$$

$$S = r_{eGaIn}^2 \pi$$

$$r_x = (r_{container} - r_{eGaIn}) \sin(\alpha) \quad (4)$$

$$r_y = \sqrt{r_{eGaIn}^2 - r_x^2} \quad (5)$$

$$S_2 = S \frac{2 \tan^{-1}\left(\frac{r_y}{r_x}\right)}{2\pi} - r_x r_y \quad (6)$$

Figure 5:
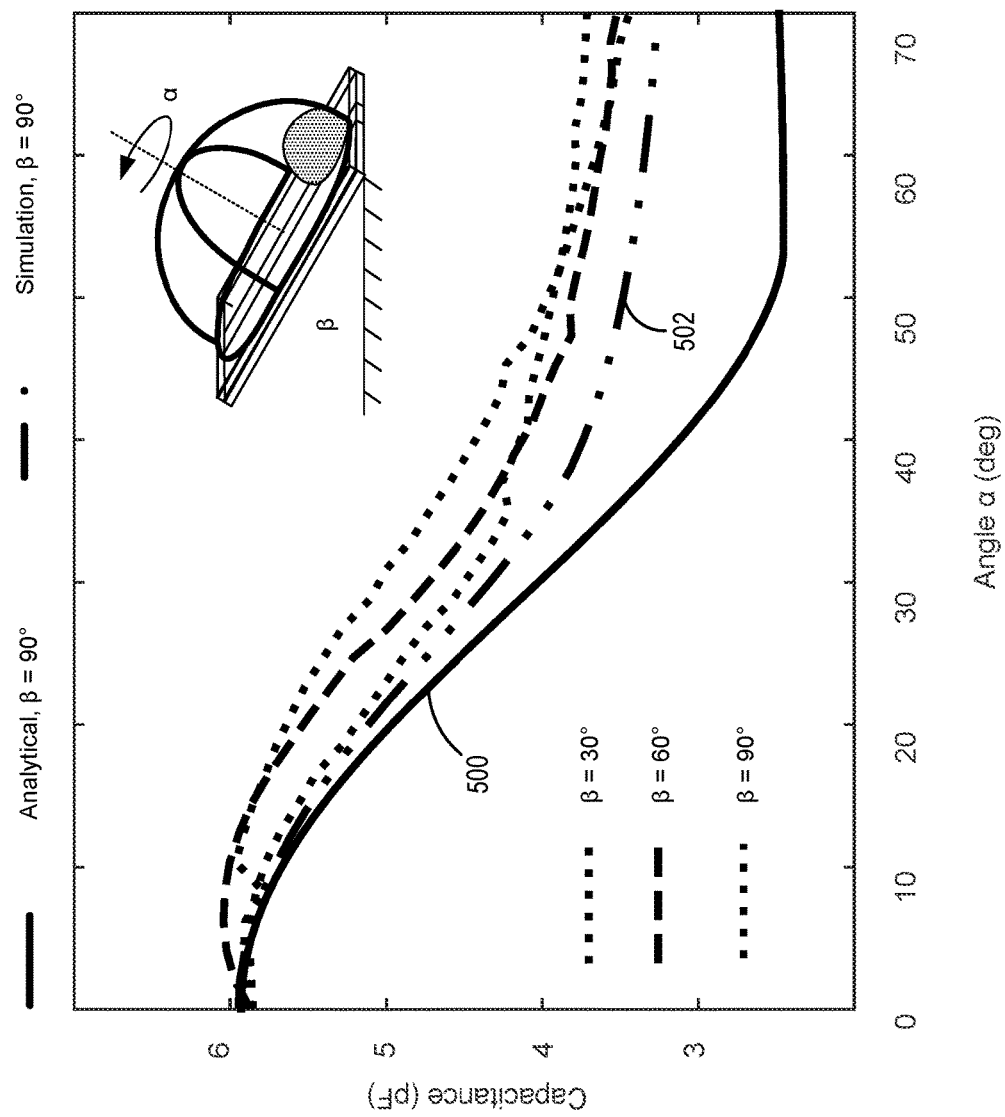
FIG. 5 shows a graph illustrating an example change of capacitance as a function of angle of a liquid metal droplet with respect to a matrix containing the liquid metal droplet.

FIG. 5 shows a graphical representation of capacitance of the sensor arrangement of FIGS. 4A, 4B and 10 as a function of angle α of FIG. 4B. Curve 500 in FIG. 5 corresponds to the $C_{total}$ determined using the equations above, and omits $C_{liquid}$ and $C_{pass}$. Curve 500 as depicted has been translated up to 6 pF such that it matches measurements at α=0°. Simulation is represented by the dot-dot-dash curve 502, and the remaining curves show measurements with varying tilt β. The simulation includes the influence of $C_{liquid}$ and $C_{pass}$. The graph shows the measured behavior and explains the influence of $C_{liquid}$ on the overall capacitance of the sensor, $C_{total}$. The difference between the analytical model and the measurements may be accounted for by the electrical fringing field, which forms through the surrounding liquid matrix. The liquid metal droplet modifies the electrical fringing field, which results in a change of capacitance, similar to how a human finger changes the capacitance on a capacitive touch screen, for example.

Figure 6:
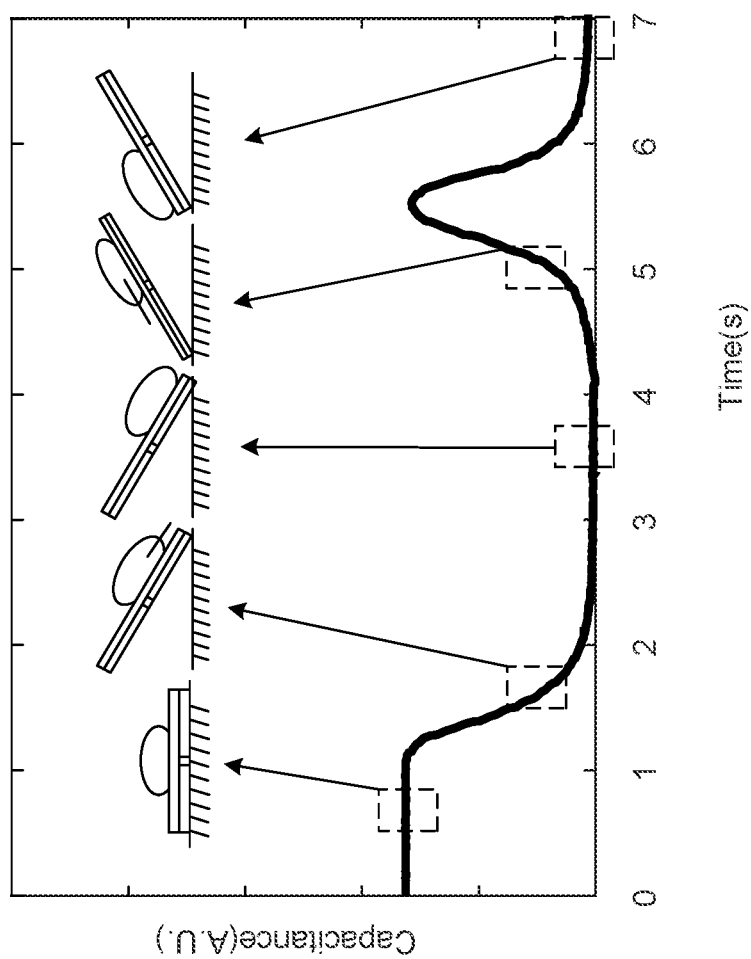
FIG. 6 shows a representation of capacitance of a sensor as a function of time as a liquid metal droplet slides across two metal plates based upon varying movements.

FIG. 6 shows total capacitance in picofarads (pF) as a function of number of samples over time (1 second for every 20 samples) as the liquid metal droplet slides across the two metal plates based upon varying movements.

Figure 7:
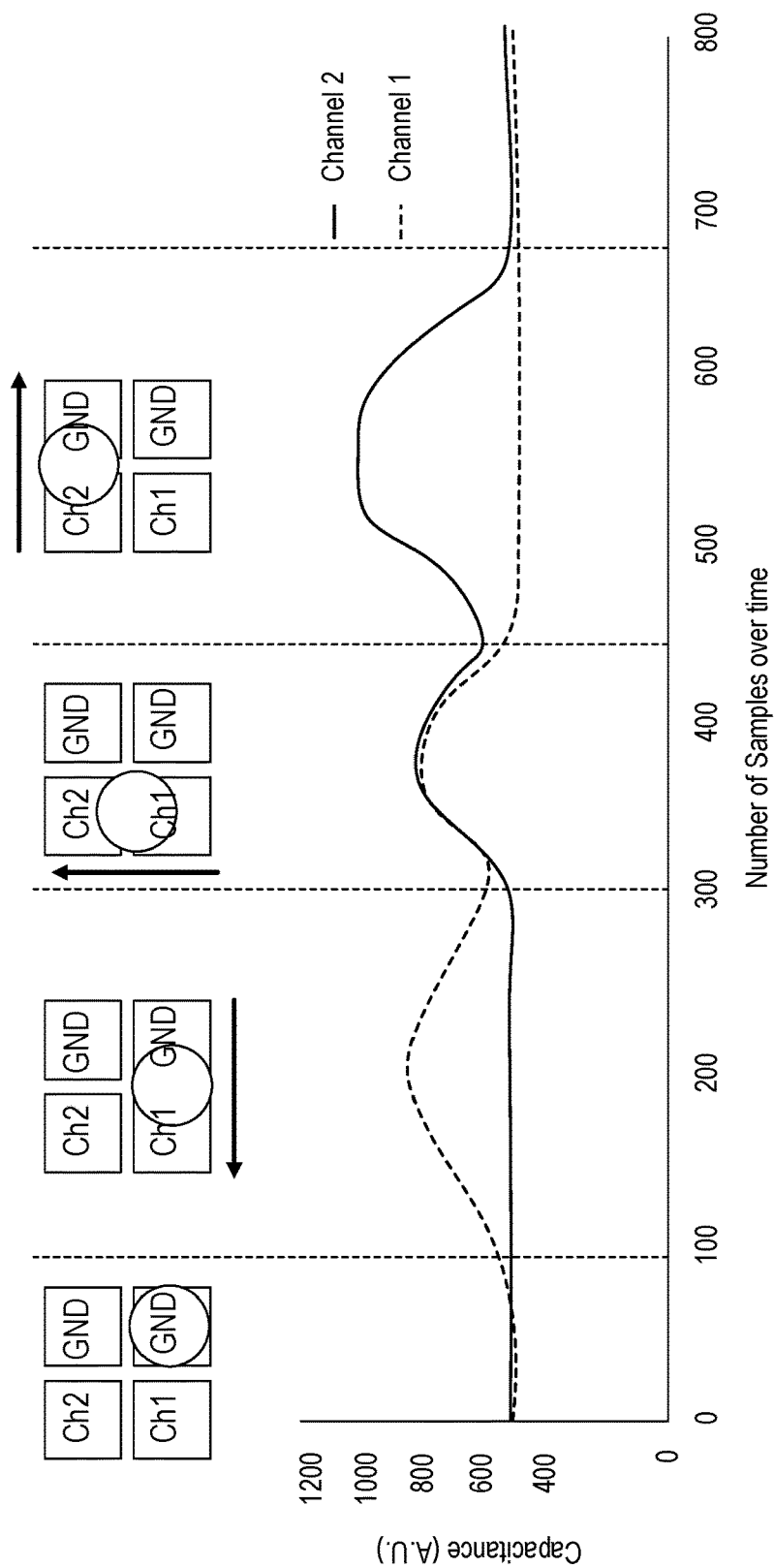
FIG. 7 shows an example of a tilt sensor comprising four electrodes and illustrates changes in capacitance of the sensor as a function of time in response to movement of the sensor.

FIG. 7 shows another example liquid metal tilt sensor, in which a liquid metal droplet slides over four electrodes, rather than just two. In this configuration, the tilt sensor may detect tilt in directions along two axes. FIG. 7 also shows capacitance measured via two channels, one for each axis of tilt, as a function of time.

Figure 8:
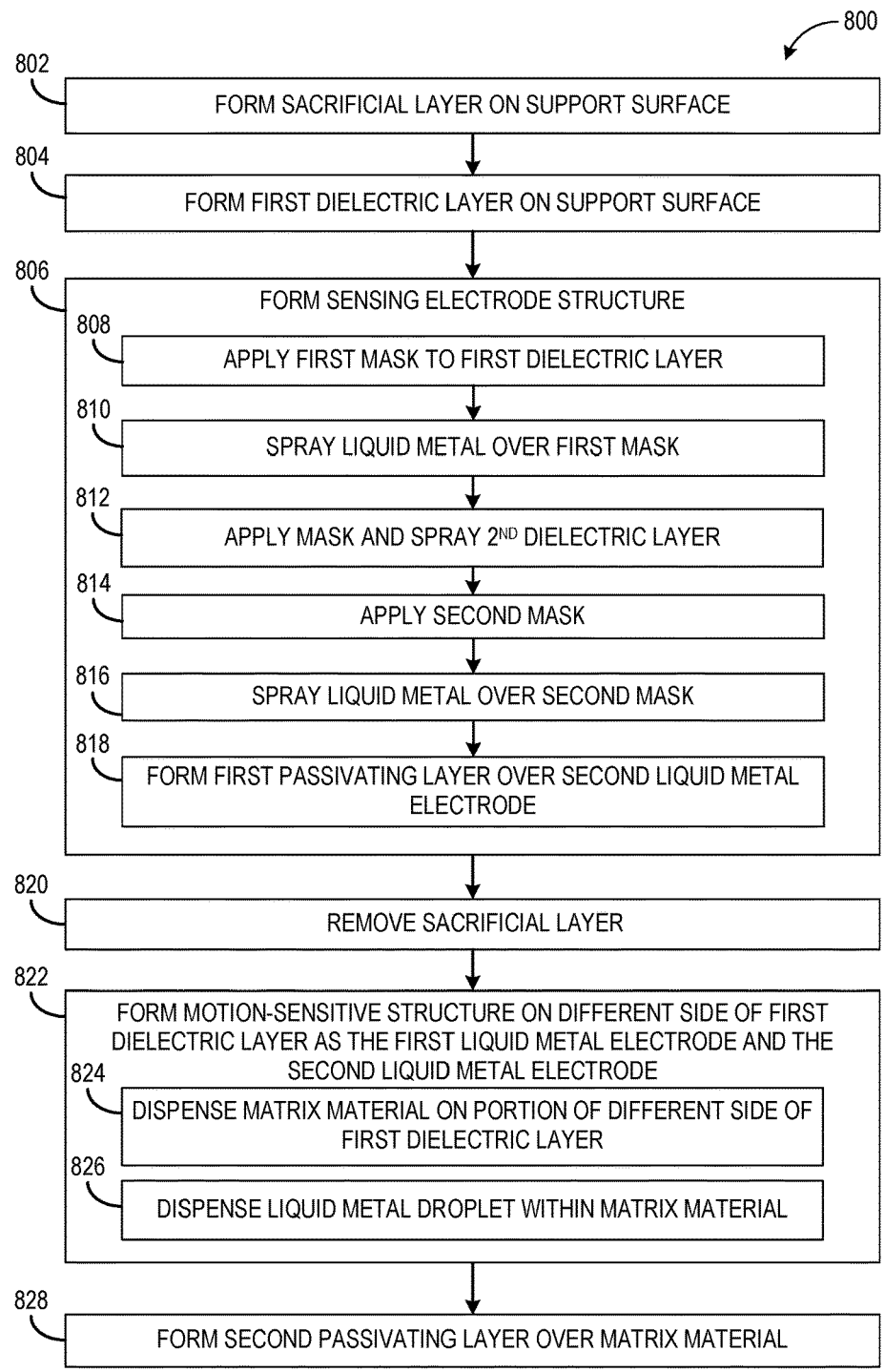
FIG. 8 shows a block diagram of an example method of making a motion sensor as disclosed herein.

FIG. 8 is a block diagram showing an example method 800 of making a motion sensor as disclosed herein. Method 800 includes, at 802, forming a sacrificial layer on a support surface, such as a semiconductor wafer or other surface having desired chemical and physical properties. Method 800 further includes, at 804, forming a first dielectric layer on the support surface, such as by spin coating a dielectric material onto the support surface. Method 800 also includes, at 806, forming a sensing electrode structure. The sensing electrode structure may be formed by applying a first mask to the first dielectric layer, at 808, and spraying liquid metal over the first mask to pattern a first liquid metal electrode, at 810. Optionally, at 812, a second dielectric layer may be formed by applying a different mask for the dielectric layer and spraying a dielectric material over the mask, e.g. using a same or different dielectric material as the first dielectric layer over the first liquid metal electrode.

The sensing electrode structure may further be formed by applying a second mask, at 814, and spraying liquid metal over the second mask to pattern the second liquid metal electrode, at 816. In some examples, a dielectric layer may be applied between the first liquid metal patterning step and the second liquid metal patterning step, as described above. At 818, a first passivating layer is formed over the second liquid metal electrode. The passivating layer may be formed from any suitable material, which may be the same or different as other dielectric layers in the sensor. In some examples, one or more of the patterning steps described above also may be used to form an RF antenna, and/or other electrical components.

Method 800 further includes, at 820, dissolving the sacrificial layer to release the support surface. At this point, various different modifications may be made to the current sensor structure to adapt the sensor structure for different sensor uses. For example, to form the liquid metal droplet-based examples described above, method 800 next includes, at 822, forming a motion-sensitive structure on a different side of the first dielectric layer as the first liquid metal electrode and the second liquid metal electrode. Forming the motion-sensitive structure may include, at 824, dispensing a matrix material on a portion of the different side of the first dielectric layer, and at 826, dispensing a liquid metal droplet within the matrix material.

After forming the motion-sensitive structure, method 800 includes, at 828, forming a second passivating layer over the matrix and liquid metal droplet.

In some examples, one dielectric layer may be formed without forming a second dielectric layer. For example, the first and second liquid metal electrodes may be formed on a support structure, a dielectric layer may be formed over both electrodes, and the liquid metal droplet may be formed on the opposing side of the dielectric layer to form the capacitive sensor. Likewise, in some examples, the sensing electrode structure may be formed from a non-liquid phase material (e.g. a solid metal conductor or a printed conductive ink), instead of a liquid metal.

Another example provides a sensor, comprising a sensing electrode structure and a motion-responsive structure in capacitive communication with the sensing electrode structure, the sensing electrode structure and the motion-responsive structure being separated by a first dielectric layer, the motion-responsive structure comprising a liquid metal droplet contained within a matrix in which the liquid metal droplet is movable based upon movement of the sensor, and the sensing electrode structure comprising a first liquid metal electrode, and a second liquid metal electrode spaced from the first liquid metal electrode. The sensor may additionally or alternatively include a second dielectric layer between the first liquid metal electrode and the second liquid metal electrode. The sensor may additionally or alternatively include a first passivating layer on a first side of the sensor, and a second passivating layer on a second side of the sensor. One or more of the first liquid metal electrode and the second liquid metal electrode may additionally or alternatively include gallium and indium. The matrix may additionally or alternatively include a surfactant. The matrix may additionally or alternatively include glycerol. The sensor may additionally or alternatively include a radiofrequency antenna in communication with the first liquid metal electrode and the second liquid metal electrode. The radiofrequency antenna may additionally or alternatively be formed at least partially from liquid metal. The sensor may additionally or alternatively be stretchable.

Another example provides a method of making a motion sensor, comprising forming a sensing electrode structure, and forming a motion-responsive structure separated from the sensing electrode structure by a first dielectric layer, the motion-responsive structure comprising a liquid metal droplet within a matrix in which the liquid metal droplet can move in response to motion of the sensor, and forming a passivating layer over the motion-sensing structure. Forming the sensing electrode structure may additionally or alternatively include forming a first liquid metal electrode and forming a second liquid metal electrode via spraying the liquid metal onto one or more masks defining the sensing electrode structure. In this example, a first mask may additionally or alternatively be used to define the first liquid metal electrode and a second mask may additionally or alternatively be used to define the second liquid metal electrode. Forming the motion-responsive structure may additionally or alternatively include dispensing a matrix material onto a portion of the different side of first dielectric layer as the first liquid metal electrode and the second liquid metal electrode, and dispensing the liquid metal droplet within the matrix material.

Another example provides a method of making a sensor, comprising forming a first dielectric layer, forming a first electrode and a second electrode by applying one or more masks and spraying a liquid metal through one or more openings in the one or more masks to pattern the first electrode and the second electrode, and passivating the first electrode and the second electrode with one or more passivating layers. The first dielectric layer may additionally or alternatively be formed on a support surface, and the method may additionally or alternatively include forming a sacrificial layer on the support surface prior to forming the first dielectric layer, and forming the first dielectric layer over the sacrificial layer, and dissolving the sacrificial layer prior to forming the motion-responsive structure. The method may additionally or alternatively include forming a second dielectric layer between the first and second electrodes. The method may additionally or alternatively include forming a motion-responsive structure on a different side of the first dielectric layer as the first liquid metal electrode and the second liquid metal electrode, the motion-responsive structure comprising a liquid metal droplet within a matrix in which the liquid metal droplet can move in response to motion of the sensor, and forming a second passivating layer over the matrix. Forming the motion-responsive structure may additionally or alternatively include dispensing a matrix material onto a portion of the different side of first dielectric layer as the first liquid metal electrode and the second liquid metal electrode, and dispensing the liquid metal droplet within the matrix material. The method may additionally or alternatively include forming a radiofrequency antenna coupled with the first electrode and second electrode via spray coating of a liquid metal using masking to define an antenna pattern.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A sensor, comprising:
a sensing electrode structure and a motion-responsive structure in capacitive communication with the sensing electrode structure, the sensing electrode structure and the motion-responsive structure being separated by a first dielectric layer,
the motion-responsive structure comprising a liquid metal mass within a matrix in which the liquid metal mass is movable based upon movement of the sensor, and
the sensing electrode structure comprising
a first electrode, and a second electrode spaced from the first electrode to form a capacitor.

2. The sensor of claim 1, further comprising a second dielectric layer between the first electrode and the second electrode.

3. The sensor of claim 1, further comprising a first passivating layer on a first side of the sensor, and a second passivating layer on a second side of the sensor.

4. The sensor of claim 1, wherein one or more of the first electrode and the second electrode comprises a liquid metal comprising gallium.

5. The sensor of claim 1, wherein the matrix comprises a surfactant.

6. The sensor of claim 1, wherein the matrix comprises glycerol.

7. The sensor of claim 1, further comprising a radiofrequency antenna in communication with the first electrode and the second electrode.

8. The sensor of claim 7, wherein the radiofrequency antenna is formed at least partially from liquid metal.

9. The sensor of claim 1, wherein the sensor is stretchable.

* * * * *